United States Patent [19]

Antoniades et al.

[11] Patent Number: 4,983,581
[45] Date of Patent: Jan. 8, 1991

[54] WOUND HEALING COMPOSITION OF IGF-I AND TGF-$\beta$

[75] Inventors: Harry N. Antoniades, Newton; Samuel E. Lynch, Jamaica Plain, both of Mass.

[73] Assignees: Institute of Molecular Biology, Inc., Boston; President and Fellows of Harvard College, Cambridge, both of Mass.

[21] Appl. No.: 196,975

[22] Filed: May 20, 1988

[51] Int. Cl.$^5$ ............................................. A61K 37/36
[52] U.S. Cl. ..................................... 514/12; 424/532; 514/2; 514/21; 530/399
[58] Field of Search ................ 514/2, 12, 21; 500/399; 424/101

[56] References Cited

U.S. PATENT DOCUMENTS

| | | |
|---|---|---|
| 4,085,204 | 4/1978 | Wacker et al. |
| 4,350,687 | 9/1982 | Lipton et al. ......................... 424/177 |
| 4,479,896 | 10/1984 | Antoniades . |
| 4,604,234 | 8/1986 | Fujii et al. ................................. 514/2 |
| 4,702,908 | 10/1987 | Thorbecke et al. ................... 424/88 |
| 4,738,921 | 4/1988 | Belagaje et al. ..................... 435/69.7 |
| 4,742,003 | 5/1988 | Derynck et al. ....................... 435/68 |
| 4,745,179 | 5/1988 | Ueda et al. ............................ 530/350 |

FOREIGN PATENT DOCUMENTS 0267015  4/1987  European Pat. Off. .

OTHER PUBLICATIONS

Betsholtz et al., "Growth Factor-Induced Proliferation of Human Fibroblasts in Serum-Free Culture Depends on Cell Density and Extracellular Calcium Concentration," J. of Cellular Physio., 118: 203-210 (1984).
Canalis, "Effect of Platelet-Derived Growth Factor on DNA and Protein Synthesis in Cultured Rat Calvaria," Metabolism, 30: 970-975 (1981).
Clemmons et al., "Somatomedin-C and Platelet-Derived Growth Factor Stimulate Human Fibroblast Replication," J. of Cellular Physio., 106: 361-367 (1981).
Stiles et al., "Dual Control of Cell Growth by Somatomedins and Platelet Derived Growth Factor," Proc. Natl. Acad. Sci. USA, 76: 1279-1283, 1979.
Tashjian et al., "Platelet-Derived Growth Factor Stimulates Bone Resorption via a Prostaglandin-Mediated Mechanism" Endocrinology, 111: 118-124 (1982).
Van Wyk et al., "Role of Somatomedin in Cellular Proliferation in *The Biology of Normal Human Growth*", edited by M. Ritzen et al., Raven Press, pp. 223-239 (1981).
Shipley et al., "Reversible Inhibition of Normal Human Prokeratinocyte by Type B Transforming Growth Factor-Growth Inhibitor in Serum-Free Medium," Cancer Research, 46: 2068-2071 (1986).
Sporn et al., "Polypeptide Transforming Growth Factors Isolated from Bovine Sources and Used for Wound Healing in Vivo," Science, 219: 1329-1331 (1983).
Sporn et al., "Repair of Tissue in Animal", U.S. Ser. No. 468,590, dated filed 2/22/83.
Rinderknecht et al., "Primary Structure of Human Insulin-Like Growth Factor II," Proc. Natl. Acad. Sci. USA, 89: 283-286 (1978).
Ross et al., "The Biology of Platelet-Derived Growth Factor", Cell, 46 : 155-169 (1986).
Schultz et al., "Epithelial Wound Healing Enhanced by Transform Growth Factor," Chemical Abstracts, 106: 96915h (1987).
Leitzel et al., "Growth Factors and Wound Healing in the Hamster," J. Dermatol. Surg. Oncol., 11: 617-621 (1985).
Lynch et al., "Role of Platelet-Derived Growth Factor in Wound Healing: Synergistic Effects with Other Growth Factors," Proc. Natl. Acad. Sci. USA, 84: 7696-7700 (1987).
Michaeli et al., "The Role of Platelets in Wound Healing: Demonstration of Angiogenic Activity," *Soft and Hard Tissue Repair*, Hunt et al., eds., Praeger Scientific, 1984, pp. 380-394.
Grotendorst et al., "Stimulation of Granulation Tissue Formation by Platelet-Derived Growth Factor in Normal and Diabetic Rats," J. Clin. Invest., 76: 2323-2329 (1985).
Hebda, "The Effects of Peptide Growth Factors on Epidermal Outgrowth in an in vitro Wound Healing Model", J. of Cell Biology, 107: p. 46A (1989).
Heldin et al., "Growth of Normal Human Glial Cells in a Defined Medium Containing Platelet-Derived Growth Factor," Proc. Natl. Acad. Sci. USA, 77: 6611-6615 (1980).
Computer Print Out of Various Patent Abstracts, (Pfizer).
Grotendorst, "Can Collagen Metabolism by Controlled"?, J. of Trauma 24: 549-552 (1984).
Grotendorst et al., "Molecular Mediators of Tissue Repair," in *Soft and Hard Tissue Repair*, Hunt et al., eds., Praeger Scientific, 1984, pp. 20-40.

*Primary Examiner*—Howard E. Schain
*Attorney, Agent, or Firm*—Fish & Richardson

[57] ABSTRACT

Healing an external wound of a mammal by administering to the mammal a composition containing purified Insulin-like growth factor-1 and purified transforming growth factor beta.

8 Claims, No Drawings

WOUND HEALING COMPOSITION OF IGF-I AND TGF-β

BACKGROUND OF THE INVENTION

This invention relates to healing wounds.

Growth factors are polypeptide hormones which stimulate a defined population of target cells. Examples of growth factors include platelet-derived growth factor (PDGF), insulin-like growth factor (IGF-I), transforming growth factor beta (TGF-β), transforming growth factor alpha (TGF-α), epidermal growth factor (EGF), and fibroblast growth factor (FGF).

TGF-β is a multifunctional regulatory polypeptide synthesized by many cell types and sequestered in human platelets in amounts similar to PDGF. The in vitro biological effects of TGF-β are dependent upon the presence of other growth factors: TGF-β in the presence of PDGF stimulates fibroblast growth, and in the presence of EGF inhibits fibroblasts (Roberts, et al. Proc. Natl. Acad. Sci, USA 82:119). TGF-β inhibits proliferation of epithelial cells in vitro (Shipley et al., 1986, Cancer Res. 46:2068), and in vivo stimulates DNA, total protein, and collegen synthesis when injected into wound chambers (Sporn et al., 1986, Science 219:1329). The breaking strength of incisional wounds increases in a dose dependent manner after application of TGF-β (Mustoe, et al., Science 237:1333).

IGF-1 is synthesized de novo in the liver and secreted into the plasma. In vitro, IGF-1 can promote DNA synthesis in both mesenchymal and epithelial cells (Van Wyk 1984, Hormonal Proteins and Peptides, Li, ed.). Addition of IGF-1 in vivo by itself does not promote wound healing, but when added with PDGF the combination stimulates connective tissue and epithelial proliferation (Lynch, et al., 1987, Proc. Natl. Acad. Sci., USA 84:7696).

SUMMARY OF THE INVENTION

In general, the invention features healing an external wound in a mammal, e.g., a human patient, by applying to the wound an effective amount of a composition that includes a combination of purified TGF-β and purified IGF-1. Preferably, the TGF-β is human TGF-β, but can also be of another mammalian species, e.g., porcine. The TGF-β can be isolated from natural sources (e.g., platelets) or, more preferably, produced by recombinant cells. The IGF-1 can be produced using recombinant DNA technology or solid phase peptide synthesis.

The composition of the invention aids in healing the wound, at least in part, by promoting the growth of epithelial and connective tissue and the synthesis of total protein and collagen. Wound healing using the composition of the invention is more effective than that achieved in the absence of treatment (i.e., without applying exogenous agents) or by treatment with purified IGF-1 alone, or purified TGF-β alone.

In preferred embodiments of the invention, the composition is prepared by combining, in a pharmaceutically acceptable carrier substance, e.g., commercially available inert gels or liquids (e.g., saline supplemented with albumin or methyl cellulose), purified IGF-1 and TGF-β (both of which are commercially available). Most preferably purified IGF-1 and TGF-β are combined in a weight-to-weight ratio of between 1:4 and 4:1, preferably between 1:2 and 2:1, and more preferably 1:1 or 2:1. The purified TGF-β may be obtained from human platelets or by recombinant DNA technology. Thus, by the term "TGF-β" we mean both platelet-derived and recombinant materials of mammalian, preferably primate, origin; most preferably, the primate is a human, but can also be a chimpanzee or other primate. Recombinant TGF-β can be recombinant monomer or homodimer, made by inserting into cultured prokaryotic or eukaryotic cells a DNA sequence encoding a subunit, and then allowing the translated subunits to be processed by the cells to form a homodimer.

The term "purified" as used herein refers to IGF-1 or TGF-β which, prior to mixing with the other, is 95% or greater, by weight, IGF-1 or TGF-β, i.e., is substantially free of other proteins, lipids, and carbohydrates with which it is naturally associated.

A purified protein preparation will generally yield a single major band on a polyacrylamide gel for each IGF-1 or TGF-β component. Most preferably, the purified IGF-1 or TGF-β used in the composition of the invention is pure as judged by amino-terminal amino acid sequence analysis.

The composition of the invention provides a fast, effective method for healing external wounds of mammals, e.g., bed sores, lacerations and burns. The composition enhances connective tissue formation compared to natural healing (i.e., with no exogenous agents added) or pure IGF-1 or TGF-β alone. Unlike pure TGF-β alone, the composition promotes a significant increase in both new epithelial tissue and connective tissue. The epithelial layer obtained is thicker than that created by natural healing or by TFG-β alone, and also contains more epithelial projections connecting it to the new connective tissue; it is thus more firmly bound and protective.

Other features and advantages of the invention will be apparent from the following description of the preferred embodiments thereof, and from the claims.

DESCRIPTION OF THE PREFERRED EMBODIMENTS

We now describe preferred embodiments of the invention.

External wounds, e.g., bed sores and burns, are treated, according to the invention, with IGF-1/TGF-β. Recombinant human IGF-1 is commercially available from Amgen Biologicals (Thousand Oaks, Calif.). Purified human and porcine TGF-β are commercially available from R&D Systems, Inc. (Minnesota, MN).

TGF-β was purified from human or porcine platelets by the method of Assoian (1983, J. Biol. Chem. 258: 7155). Briefly, platelet-rich plasma (20–30 units, 2–5 days old) was centrifuged (3200×g 30 min, at 4° C.) to remove plasma proteins. The platelets were then washed twice in 500ml portions of Tris-HCl/citrate buffer, and recentrifuged. The washed platelets were then added to a solution of acid ethanol and then immediately extracted in a homogenizer. After incubation overnight at 4° C., precipitated proteins were removed by centrifugation and the supernatant adjusted to pH 3 using NH$_4$OH. TGF-β was precipitated by addition of ethanol (2 volumes at 0° C.) and ethyl ether (4 volumes at 0° C.). The precipitate was collected by centrifugation and suspended in 1M acetic acid (10ml). The supernatant was separated from the precipitate by centrifugation and placed on a Bio-Gel P60 gel filtration column (4.4×115 cm), with a flow rate of 20ml/hr, eguilibrated in 1M acetic acid. Five milliliter fractions were collected and assayed for biological activity using growth inhibition of BALB/MK cells and anchorage-independent growth of non-neoplastic NRK fibroblasts. Fractions containing peak activity were pooled, lyophilized, and redissolved in 0.5ml or 1M acetic acid containing 8M ultra-pure urea (Schwartz/Mann) and gel filtered at a flow rate of 3ml/hr on a Bio-Gel P60 column (1.6×85cm). Aliquots or column fractions were tested for TGF-$\beta$ activity as described above. Fractions containing peak TGF-$\beta$ activity were pooled, dialized against 1M acetic acid to remove urea, and added to a C-18 (synchropak) HPLC column in 0.1% triflouroacetic acid and eluted with a 20–50% acetonitrile gradient. Biologically active fractions were pooled, and final purity checked by SDS-PAGE and amino acid analysis for known properties of TGF-$\beta$.

Recombinant TGF-$\beta$ can be prepared by standard techniques. For example, oligonucleotide probes designed on the basis of the protein sequence of TGF-$\beta$ can be used for the isolation of TGF-$\beta$ exons in a human genomic DNA or a cDNA library, using the technique described in Birynch (1985, *Nature* 316: 701). The gene for TGF-$\beta$ is isolated, cloned into standard expression vectors, and transfected into mammalian cells, from which TGF-$\beta$ is then purified using standard methods.

Wound Healing

To determine the effectiveness of IGF-1/TGF-$\beta$ mixtures in promoting wound healing, the following experiments were performed.

Young white Yorkshire pigs (Parson's Farm, Hadley, Mass.) weighing between 10 and 15 kg were fasted for at least 6 hours prior to surgery and then anesthetized. Under aseptic conditions, the back and thoracic areas were clipped, shaved, and washed with mild soap and water. The area to be wounded was then disinfected with 70% alcohol. Wounds measuring 1 cm x 2 cm were induced at a depth of 0.5 mm using a modified Castroviejo electrokeratome (Storz, St. Louis, Mo, as modified by Brownells, Inc.). The wounds resulted in complete removal of the epithelium, as well as a portion of the underlying dermis (comparable to a second degree burn injury). Individual wounds were separated by at least 15 mm of unwounded skin. Wounds receiving identical treatment were organized as a group and separated from other groups by at least 3 cm. Wounds receiving no growth factor treatment were separated from wounds receiving such treatment by at least 10 cm.

The wounds were treated directly with a single application of the following growth factors suspended in biocompatible gel: (1) 500 ng pure human or porcine TGF-$\beta$; (2) 500 ng pure recombinant IGF-1 alone; (3) 500 ng human or porcine TGF-$\beta$ plus 500 ng pure recombinant IGF-1.

Following wounding, biopsy specimens were taken on days 3 through 10. Biopsy specimens for histologic evaluation were taken as wedges approximately 3 mm deep and placed in 10% formalin. Specimens for biochemical analysis were obtained using an electrokeratome. The final dimensions of the specimens were 1.5 mm×10 mm×1.5 mm. Three specimens per wound were collected for biochemical analysis. Following collection, the specimens ere frozen in liquid Nitrogen and stored at −80° C.

Histologic Evaluation

Histologic specimens were prepared using standard paraffin impregnating and embedding techniques. Four micron sections were made and stained using filtered Harris hemotoxylin and alcoholic eosin; they were then observed under a microscope. Computer-aided morphometric analyses were performed. The area of the new epithelial and connective tissue layers were assessed with the aid of a customized program (need details) for determining areas of histological specimens.

Collagen Determination

The specimens for biochemical analysis were thawed and the newly synthesized wound tissue dissected from the surrounding tissue under a dissecting microscope. The samples were hydrolyzed in 6M HCl at 120° C. for 18 hours in sealed ampoules. Assay of the hydrolysate for hydroxyproline, an amino acid unique to collagen was then performed using the technique of Switzer and Summer, 1971, *Anal. Biochem.* 39:487.

Results

The results from histologic evaluation indicated that wounds treated with TGF-$\beta$ had a thinner epithelial layer than wounds receiving no treatment. In contrast, wounds treated with the combination of purified human or porcine TGF-$\beta$ and recombinant human IGF-1 had thicker connective tissue and epithelial layers, and more extensive epithelial projections connecting these layers, than wounds receiving no treatment, human or porcine TGF-$\beta$ alone, or pure IGF-1 alone. The IGF-1 plus TGF-$\beta$-treated wounds also had greater total collagen content, as indicated by increased hydroxyproline, than wounds treated with TGF-$\beta$ alone, IGF-1 alone, or gel alone.

Dosage

To determine the appropriate dosage of purified TGF-$\beta$, the above-described experiments were repeated except that the wounds were treated with 2.5 ng, 5.0 ng, and 10 ng of purified TGF-$\beta$ per square millimeter of wound dispersed in 30 $\mu$l of biocompatible gel. The results showed that optimum effects were produced when the TGF-$\beta$ content of a IGF-1/TGF-$\beta$ mixture was 5.0 ng/mm$^2$ or higher.

To determine the optimal ratio of IGF-1 to TGF-$\beta$, combinations in which the weight to weight ratio of IGF-1 to TGF-$\beta$ ranged from 1:10 to 25:1 were evaluated as described above. Optimum results were achieved with a ratio of between 1:2 and 2:1.

OTHER EMBODIMENTS

Other embodiments are within the following claims. For example, IGF-1 and TGF-$\beta$ can be obtained by standard recombinant DNA technology using nucleic acid having a base sequence identical to that of the naturally occuring gene encoding IGF-1 or TGF-$\beta$ in a human or other mammal. Further, this nucleic acid may be modified by conservative base substitutions such that it encodes the same amino acid sequence of naturally occuring IGF-1 or TGF-$\beta$; or modified with base substitutions which encode a different amino acid sequence to that naturally occuring, but the protein product of which has substantially the same wound healing properties as the naturally occuring proteins.

We claim:

1. A method for healing an external wound of a mammal comprising applying to said wound a wound-healing amount of a composition consisting essentially or purified Insulin-like growth factor-1 and transforming growth factor beta.

2. The method of claim 1 wherein the weight to weight ratio of said Insulin-like growth factor-1 to said transforming growth factor beta in said composition is between 1:4 and 25:1.

3. The method of claim 2 wherein said ratio is between 1:2 and 10:1.

4. The method of claim 3 wherein said ratio is about 1:2 or 2:1.

5. A wound healing composition consisting essentially of purified Insulin-like Growth Factor-1 and purified transforming growth factor beta, in a weight to weight ratio of 1:4 to 25:1.

6. The composition of claim 5 wherein said ratio is between 1:2 and 10:1.

7. The composition of claim 6 wherein said ratio is about 1:2 or 2:1.

8. A method for preparing a composition for healing wounds, consisting essentially of mixing purified Insulin-like Growth Factor-1 and purified transforming growth factor beta in a weight to weight ratio of 1:4 to 25:1.

* * * * *